(12) United States Patent
Overes

(10) Patent No.: US 8,945,136 B2
(45) Date of Patent: Feb. 3, 2015

(54) INTRAMEDULLARY NAIL AIMING DEVICE

(75) Inventor: Tom Overes, Oberdorf (CH)

(73) Assignee: DePuy Synthes Products, LLC, Raynham, MA (US)

( * ) Notice: Subject to any disclaimer, the term of this patent is extended or adjusted under 35 U.S.C. 154(b) by 308 days.

(21) Appl. No.: 13/089,846

(22) Filed: Apr. 19, 2011

(65) Prior Publication Data

US 2011/0270328 A1    Nov. 3, 2011

Related U.S. Application Data

(60) Provisional application No. 61/325,913, filed on Apr. 20, 2010.

(51) Int. Cl.
*A61B 17/58* (2006.01)
*A61B 17/60* (2006.01)
*A61F 2/00* (2006.01)
*A61B 17/17* (2006.01)

(52) U.S. Cl.
CPC ..... *A61B 17/1725* (2013.01); *A61B 2017/1778* (2013.01)
USPC .............................................. 606/98; 606/96

(58) Field of Classification Search
CPC .................................................. A61B 17/1725
USPC ............................................ 606/96, 280, 98
See application file for complete search history.

(56) References Cited

U.S. PATENT DOCUMENTS

| 4,541,424 | A | 9/1985 | Grosse et al. |
| 4,976,713 | A | 12/1990 | Landanger et al. |
| 7,311,710 | B2 | 12/2007 | Zander |
| 2006/0264946 | A1* | 11/2006 | Young ............................. 606/69 |
| 2008/0039857 | A1 | 2/2008 | Giersch et al. |
| 2008/0058829 | A1 | 3/2008 | Buscher et al. |
| 2008/0281331 | A1 | 11/2008 | Fritzinger et al. |
| 2009/0326541 | A1* | 12/2009 | Metzinger et al. ............. 606/98 |
| 2010/0152740 | A1 | 6/2010 | O'Reilly et al. |

FOREIGN PATENT DOCUMENTS

| CN | 2394586 | 9/2000 |
| CN | 2502656 | 7/2002 |
| CN | 2624839 | 7/2004 |
| CN | 2676850 | 2/2005 |
| CN | 2812857 | 9/2006 |
| CN | 2922822 | 7/2007 |
| DE | 3245680 | 10/1983 |
| DE | 4240277 | 6/1993 |
| DE | 10110246 | 10/2002 |
| EP | 0951873 | 10/1999 |

(Continued)

*Primary Examiner* — David Bates

(74) *Attorney, Agent, or Firm* — Wayne C. Jaeschke, Jr.

(57) ABSTRACT

An aiming plate for orienting tools toward target features of an implant. The aiming plate features a first and a second surface and has a reversible attachment mechanism for attaching to an implant to orientate one of the first and second surfaces to face the implant. The aiming plate also features first and second through holes. The first through hole for receiving a tool extends along a first hole axis from the first surface to the second surface. The second through hole for receiving a tool is positioned adjacent the first through hole and extends along a second hole axis from the first surface to the second surface. The through holes arranged so that the first hole axis is divergent with respect to the second hole axis.

9 Claims, 3 Drawing Sheets

(56) References Cited

FOREIGN PATENT DOCUMENTS

| | | |
|---|---|---|
| EP | 1099413 | 5/2001 |
| EP | 1415599 | 5/2004 |
| EP | 1759643 | 3/2007 |
| WO | 92/01422 | 2/1992 |
| WO | 03/041595 | 5/2003 |

* cited by examiner

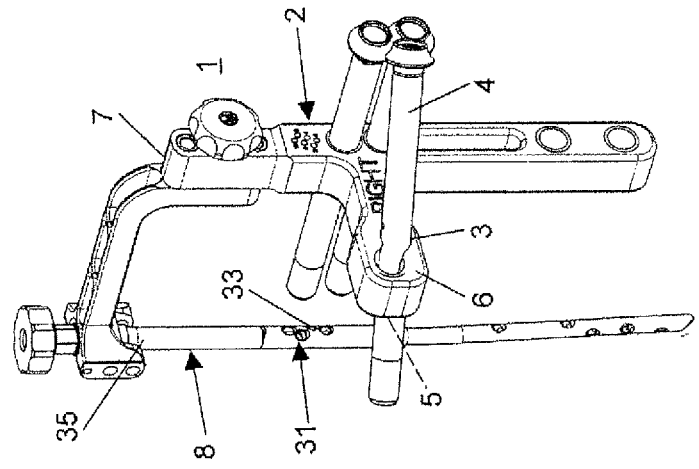
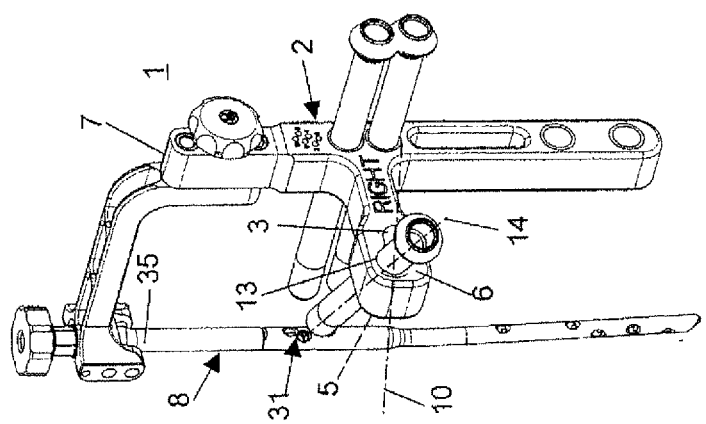
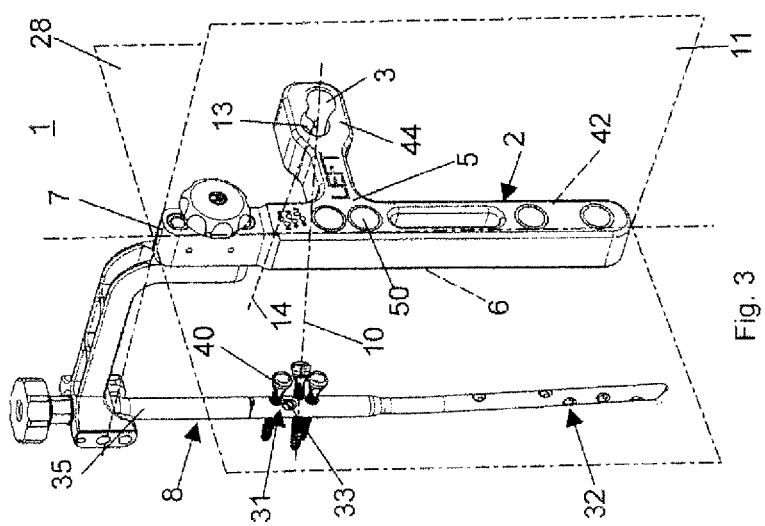

INTRAMEDULLARY NAIL AIMING DEVICE

PRIORITY CLAIM

The present application claims priority to U.S. Provisional Application Ser. No. 61/325,913 filed on Apr. 20, 2010 and entitled "Intramedullary Nail Aiming Device," the entire disclosure of which is incorporated herein by reference

FIELD OF THE INVENTION

The present invention generally relates to an aiming device for guiding a drill bit during the drilling of a hole in a bone. More particularly, the present invention relates to an intramedullary nail aiming device for drilling holes in a bone that are suitable for receiving locking screws of an intramedullary nail. Exemplary embodiments of the invention relate to a system comprising an intramedullary nail aiming device and an intramedullary nail and to a method for drilling the holes in a bone for inserting locking screws in an intramedullary nail by using the intramedullary nail aiming device.

BACKGROUND

Intramedullary nails including fixation screws inserted through the intramedullary nail in a transverse direction to lock the intramedullary nail relative to the bone are commonly known. In particular, proximal humerus nails comprise multiple fixation screws arranged at different angles relative to each other in the proximal part of the intramedullary nail to securely fixate bone fragments.

These screws are positioned in the intramedullary nail in corresponding through holes using an aiming arm or aiming block rigidly connected to the proximal end of the intramedullary nail by an intermediate member. These aiming blocks feature guiding holes aligned with the through holes in the intramedullary nail but arranged at a distance from the bone to leave space for the arm and shoulder of the patient. Generally, drilling or guiding sleeves are inserted into the holes in the aiming block drilling tools and screwdrivers guided through the sleeves are exactly aligned with the holes in the intramedullary nail. For anatomical reasons, intramedullary nails are commonly provided in "left" and "right" embodiments, i.e. in a mirrored configuration. Therefore, the aiming blocks generally feature through holes matching the left side and the right side configurations of the intramedullary nail. Because aiming blocks which preferably include radiolucent carbon fibre reinforced PEEK material are very costly, it is preferred to have only one aiming block for both configurations of the intramedullary nail. Known aiming instruments comprise aiming blocks with all the through holes for the left side and the right side configurations of the intramedullary nail in a single aiming block. These known aiming blocks can pose the risk that the wrong through holes may be used when preparing the bone, i.e. drilling the holes in the bone through which the fixation screws will be positioned. For example, a user may inadvertently drill through a hole corresponding to the "right side" configuration of the aiming device while working with a "left side" intramedullary nail. If a wrong hole is selected the drill bit will collide with the intramedullary nail and cause unacceptable debris possibly resulting in a loss of stability of the intramedullary nail and furthermore, an unnecessary hole drilled into the bone. In order to prevent this, the through holes in the aiming block are clearly marked "left" and "right" or are colour coded. In stressful situations, however, mistakes may still be made.

German Patent No. DE 101 10 246 C2 ERHARDT discloses an aiming device for a tibial locking nail which can be used for placing locking screws for the left as well as for the right tibia using the same device. However, the tibial nail used with the system of ERHARDT is of the single type and does not have different left and right side shapes.

SUMMARY OF THE INVENTION

The present invention relates to an aiming device and method for properly guiding a tool or instrument in case of a left side and a right side configuration of locking screws to be inserted in an intramedullary nail by clearly preventing from using or even making it impossible to use a wrong hole.

In a first aspect, the present invention is directed to an aiming plate for orienting tools toward target features of an implant. The aiming plate features a first and a second surface and has a reversible attachment mechanism for attaching to an implant to orientate one of the first and second surfaces to face the implant. The aiming plate also features first and second through holes. The first through hole for receiving a tool extends along a first hole axis from the first surface to the second surface. The second through hole for receiving a tool is positioned adjacent the first through hole and extends along a second hole axis from the first surface to the second surface. The through holes arranged so that the first hole axis is divergent with respect to the second hole axis.

The aiming plate may feature an attachment mechanism attachable to the implant in a first configuration in which a first surface faces the implant and in a second configuration in which a second surface faces the implant. The aiming plate may feature a first through hole for receiving a tool, which may extend along a first hole axis from the first surface to the second surface. The aiming plate may also feature a second through hole for receiving a tool, which may extend along a second hole axis from the first surface to the second surface. When an implant is coupled to the aiming plate in the first configuration, the first hole axis may be directed towards a desired target feature on the implant and the second hole axis may be directed away from the desired target feature. When an implant is coupled to the aiming plate in the second configuration, the second hole axis may be directed towards a desired target feature on the implant and the first hole axis may be directed away from the desired target feature.

The first through hole may be open to the second through hole. One or both of the first and second surfaces may feature a compound opening defined by an overlap between a first opening into the first through hole and a second opening into the second through hole.

The aiming plate may also feature third and fourth through holes. The third through hole may be for receiving a tool and may extend along a third hole axis from the first surface to the second surface. The fourth through hole may be for receiving a tool and may extend along a fourth hole axis from the first surface to the second surface. When an implant is coupled to the aiming plate in the first configuration, the third through hole axis is directed towards a second desired target feature on the implant and the fourth hole axis is directed away from the second desired target feature. When an implant is coupled to the aiming plate in the second configuration, the fourth hole axis may be directed towards a second desired target feature on the implant and the third hole axis is directed away from the second desired target feature. The first and second desired target features may be located in different regions of the implant. For example, where the implant is a proximal nail, the first desired target feature may be a locking hole in a proximal end region and the second desired target feature may be a locking hole in a distal end region.

The aiming plate may feature a first marking on the second surface, the first marking may indicate a type of implant having the desired target feature towards which the first through hole is directed in the first configuration. The aiming plate may feature a second marking on the first surface, the second marking indicating a type of implant having the desired target feature towards which the second through hole is directed in the second configuration.

Some advantages of the aiming device according to the invention are that:

the aiming device comprises a single aiming plate with the guiding holes for the left side configuration of the intramedullary nail integrated from one side and the guiding holes for the right side configuration integrated from the opposite side of the aiming plate wherein the guiding holes of the left and right side cross each other in such a manner that inserting the guide sleeves or drill bushings into the wrong hole would result therein that the guide sleeve or drill bushing is directed far beside the intramedullary nail, even missing the patient's shoulder. Therefore, if the wrong hole is taken no harm will result;

in case of a universal intramedullary nail with only one configuration for the left side or the right side bone but with different locking holes to be used when the nail is used for the left respectively the right side a surgeon can be prevented form drilling a wrong hole into the bone; and each side of the aiming plate can be largely labelled "LEFT" or RIGHT". During surgery the surgeon only once has to mount the corresponding side correctly, and only the correct through holes can be used for targeting the nail.

In an exemplary embodiment of the aiming device, the first through hole and the second through hole penetrate each other and form a compound opening. The compound opening prevents the surgeon from searching a suitable through hole, the surgeon needs only to decide into which through hole of the selected compound opening the drilling bushing is to be inserted.

In a further exemplary embodiment of the aiming device, the aiming plate comprises a first set including more than one first through holes and a second set including more than one second through holes.

In another exemplary embodiment of the aiming device, the aiming plate further comprises a lower end and a central plane extending between the upper end and the lower end and cutting the left and right side wherein the first and second hole axes of the first and second through holes of at least one compound opening are located in one plane orthogonal to the central plane. This configuration allows the advantage that identically positioned anterior and posterior locking holes in the intramedullary nail can be used in left side and right side intramedullary nails.

In yet another exemplary embodiment of the aiming device, the first and second hole axis of the first and second through hole of at least one compound opening is located in different planes orthogonal to the central plane and at different distances from the upper end of the aiming plate. Thus, a particular compound opening including first and second through holes can be arranged in the position of the problematic locking holes of a universal intramedullary nail so that a surgeon is prevented from drilling a hole into the bone coaxially with a locking hole which is problematic for anatomical reasons.

In a further exemplary embodiment of the aiming device, the aiming plate comprises a middle plane orthogonal to the central plane and at an equal distance from the left side and from the right side of the aiming plate and wherein the first and second hole axis of the first and second through hole of at least one compound opening cut the middle plane at an equal distance E from the central plane.

In yet a further exemplary embodiment of the aiming device, the first and second hole axis of the first and second through hole of at least one compound opening define a plane which is orthogonal to the central plane and orthogonal to the middle plane.

In still a further exemplary embodiment of the aiming device, the first hole axes of at least two first through holes and/or the second hole axes of at least two second through holes are not arranged in the same plane orthogonal to the central plane.

In another exemplary embodiment of the aiming device, the first hole axis of the first through hole converges towards the central plane in the direction from the left side towards the right side. By this means the advantage can be achieved that the surgeon can visually check whether the aiming plate has been correctly fixed to the intramedullary nail.

In yet another exemplary embodiment of the aiming device, the second hole axis of the second through hole diverges from the central plane in the direction from the left side towards side right side. Thus, the surgeon will visually notice at once that the aiming guide has been wrongly mounted to the intramedullary nail.

In a further exemplary embodiment of the aiming device, the first hole axis of the first through hole encloses an angle $\alpha$ with the central plane at a minimum of 5°, preferably a minimum of 15°. By this means the advantage is achieved that a sufficient angle between the inserted drilling bushings and the central plane permits a user to check whether the aiming plate is correctly fixed to the intramedullary nail. Further, the first hole axes of the first set of through holes can enclose an angle $\alpha$ with the central plane at a maximum of 70°, preferably a maximum of 45°. A typical value for the angle $\alpha$ is, for example, 30°.

In yet a further exemplary embodiment of the aiming device, the second hole axis of the second through hole encloses an angle $\beta$ with the central plane of minimum 5°, preferably minimum 15°. This configuration allows the advantage that on the one hand identically positioned locking holes in the intramedullary nail can be used in a left side and a right side intramedullary nail and on the other hand the prolongations of the second hole axes extend beside the intramedullary nail and even beside the bone where the nail is inserted so unambiguously indicating to the surgeon that the aiming guide is wrongly fixed to the intramedullary nail.

In still a further exemplary embodiment of the aiming device, the aiming plate comprises an additional compound opening of a left side through hole with a left side hole axis and a right side through hole with a right side hole axis wherein the left side hole axis and the right side hole axis are located in the central plane and diverge relative to each other in the direction from the left side towards the right side. The left side hole axis and the right side hole axis lie in or are parallel to the central plane. The left side hole axis and the right side hole axis can enclose an angle $\gamma$ at a minimum of 10°, preferably a minimum of 20°. Further, The left side hole axis and the right side hole axis can enclose an angle $\gamma$ at a maximum of 140°, preferably a maximum of 90°.

In another exemplary embodiment, the aiming device further comprises an aiming arm with a first end including a first joining means and a second end including a second joining means and wherein the first joining means is attachable to the aiming plate and the second joining means is attachable to an intramedullary nail allowing to reversibly fix the aiming plate to an intramedullary nail in an aligned left position and in an aligned right position.

In yet another exemplary embodiment of the aiming device, the aiming plate comprises a third joining means engageable with the first joining means at the aiming arm in an aligned left position and in an aligned right position.

In another exemplary embodiment, the aiming arm has a length allowing to reversibly fix the aiming plate with the middle plane at a distance A>0 from a nail axis of an intramedullary nail. In case of an intramedullary nail suitable for a fixation of a fracture of the radius the distance A is a minimum of 15 mm, preferably a minimum of 50 mm and a maximum of 200 mm, preferably a maximum of 180 mm.

In a further exemplary embodiment, the aiming device further comprises at least one drilling bushing with a front end and a rear end. The prolongation of the second hole axis can be at a distance B of minimum 10 mm, preferably minimum 30 mm from the central plane measured at the front end of the drilling bushing when inserted in one of the second through holes of the second set.

In an exemplary embodiment, the aiming device can consist of a carbon fibre reinforced PEEK, aluminum or stainless steel.

In accordance with a second aspect of the present invention, the aiming plate may be for orienting tools toward target features of an intramedullary nail, comprising an attachment mechanism at a proximal end of the aiming plate configured for attachment to a proximal end of an intramedullary nail in first a configuration in which a first surface of the aiming plate faces a nail to which it is coupled and in a second configuration in which a second surface of the aiming plate faces a nail to which it is coupled and a first compound opening extending through the aiming plate from the first surface to the second surface, the first compound opening including first and second through holes open to one another, the first through hole extending along a first hole axis configured to align with a corresponding locking hole in a nail coupled to the plate in the first configuration, the second through hole extending along a second hole axis configured to align with a corresponding locking hole in a nail coupled to the aiming plate in the second configuration, the first and second through holes being sized and shaped to receive a drill bushing therethrough and wherein, the first and second hole axes intersect one another such the first hole axis does not align with any portion of a nail coupled to the aiming plate in the second configuration and the second hole axis does not align with any portion of a nail coupled to the aiming plate in the first configuration.

In accordance with another aspect of the present invention, a system is provided for drilling the holes in a bone for inserting locking screws in an intramedullary nail by using the intramedullary nail aiming device, the system comprising an intramedullary nail aiming device according to the first or second aspect of the invention and an intramedullary nail with a nail axis.

In an exemplary embodiment of the system, the intramedullary nail comprises a fourth joining means engageable with the second joining means of the aiming arm for reversibly fixing the aiming arm to the intramedullary nail in an aligned position.

In a further exemplary embodiment of the system, the aiming arm has a length allowing to reversibly fix the aiming plate with the middle plane at a distance A of minimum 70 mm, preferably minimum 50 mm from the nail axis of the intramedullary nail.

In another exemplary embodiment of the system, the aiming arm is configured in such a manner that the nail axis extends parallel to the middle plane when the aiming device is fixed to the intramedullary nail.

In accordance with another aspect, a method is provided for aligning a through hole for receiving a tool with a desired feature of an implant. The method comprising the steps of:
   a) identifying a type of implant to be coupled to an aiming plate;
   b) determining a correct configuration of an aiming plate according to the identified implant type; and
   c) coupling the aiming plate to an implant of the identified implant type in the determined correct configuration;

Once the correct configuration is determined the aiming plate may be positioned in one of two configurations. In a first configuration, a first through hole of the aiming plate is directed towards a first target feature on a first implant type and a second through hole of the aiming plate is directed away from the first target feature. In a second configuration, the second through hole is directed towards a second target feature on a second implant type and the first through hole is directed away from the second target feature.

The method may also have a step of determining by comparing the identified implant type to a marking on the aiming plate to determine whether to couple the aiming plate in the first or in the second configuration.

The method may also have the step of recognising that the same implant type is usable as a first implant type in the first configuration and a second implant type in the second configuration. The step of determining may further have a step of identifying whether an implant is to be used in a left hand configuration or a right hand configuration, where the first target feature may be different to the second target feature on the implant.

In accordance with another aspect, a method is provided for drilling the holes in a bone for inserting locking screws in a left side or in a right side intramedullary nail by using the intramedullary nail aiming device. The method comprises the steps of:
   a) positioning the left side or the right side of the aiming plate with respect to the intramedullary nail according to which of the left side or right side configuration of the intramedullary nail is to be used during the surgical procedure;
   b) fixing the aiming plate to the intramedullary nail;
   c) inserting at least one drilling bushing into one of the through holes of the first or second set;
   d) checking whether the drilling bushing has been inserted in a correct through hole of the first set in case of a left side nail or in a correct through hole of the second set in case of a right side nail, and
      if the drilling bushing has been inserted in a wrong through hole of the second set in case of a left side nail or a wrong through hole of the first set in case of a right side nail;
         inserting the drilling bushing into the other through hole of the first respectively second set; and
         repeating step d);
   or
      if the drilling bushing has been inserted in a correct through hole of the first set in case of a left side nail or in a correct through hole of the second set in case of a right side nail, then:
   e) drilling at least one hole in a bone where the intramedullary nail is inserted by using the drilling bushing for guiding a drill bit.

In an exemplary embodiment the method further comprises the step of inserting a fixation screw through the drilling bushing.

In accordance with another aspect of the present invention, a method is provided for drilling the holes in a bone for inserting locking screws in a universal nail having only one configuration for the left and right side bone but having two locking bores or two sets of locking bores, one when implanted in a left side bone and another when implanted in a right side bone. The method comprises the steps of:
i) positioning the left side or the right side of the aiming plate with respect to the intramedullary nail according to which of the left side or right side bone is to be treated during the surgical procedure;
ii) fixing the aiming plate to the intramedullary nail;
iii) inserting at least one drilling bushing into one of the through holes of the first or second set;
iv) checking whether the drilling bushing has been inserted in a correct through hole of the first set in case of using the universal nail at a left side bone or in a correct through hole of the second set in case of using the universal nail at a right side bone, and
if the drilling bushing has been inserted in a wrong through hole of the second set in case of using the universal nail at a left side bone or in a wrong through hole of the first set in case of using the universal nail at a right side bone; inserting the drilling bushing into the other through hole of the first respectively second set;
or
if the drilling bushing has been inserted in a correct through hole of the first set in case of using the universal nail at a left side bone or in a correct through hole of the second set in case of using the universal nail at a right side bone:
v) drilling at least one hole in a bone where the intramedullary nail is inserted by using the drilling bushing for guiding a drill bit.

BRIEF DESCRIPTION OF THE DRAWINGS

A plurality of embodiments of the invention will be described in the following by way of example and with reference to the accompanying drawings in which:
FIG. 3 illustrates a perspective view of another embodiment of the aiming device according to the invention in case of an application at the left side humerus;
FIG. 4 illustrates a perspective view of the embodiment of FIG. 3 in case of an application at the right side humerus;
and
FIG. 5 illustrates a perspective view of the embodiment of FIG. 4 with one drill bushing inserted in a wrong hole.

DETAILED DESCRIPTION

Figure 1:
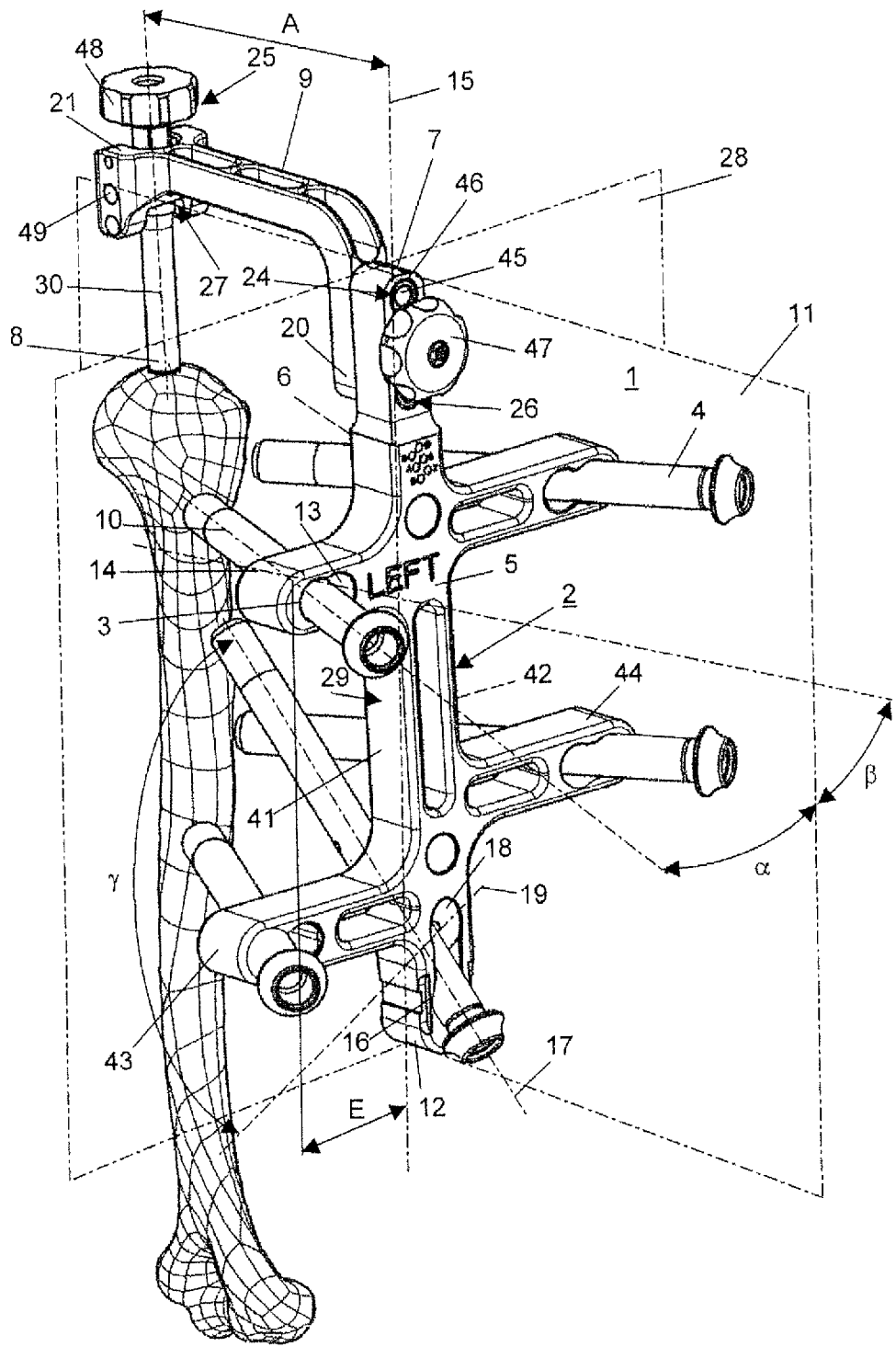
FIG. 1 illustrates a perspective view of an embodiment of the aiming device according to the invention.
Figure 2:
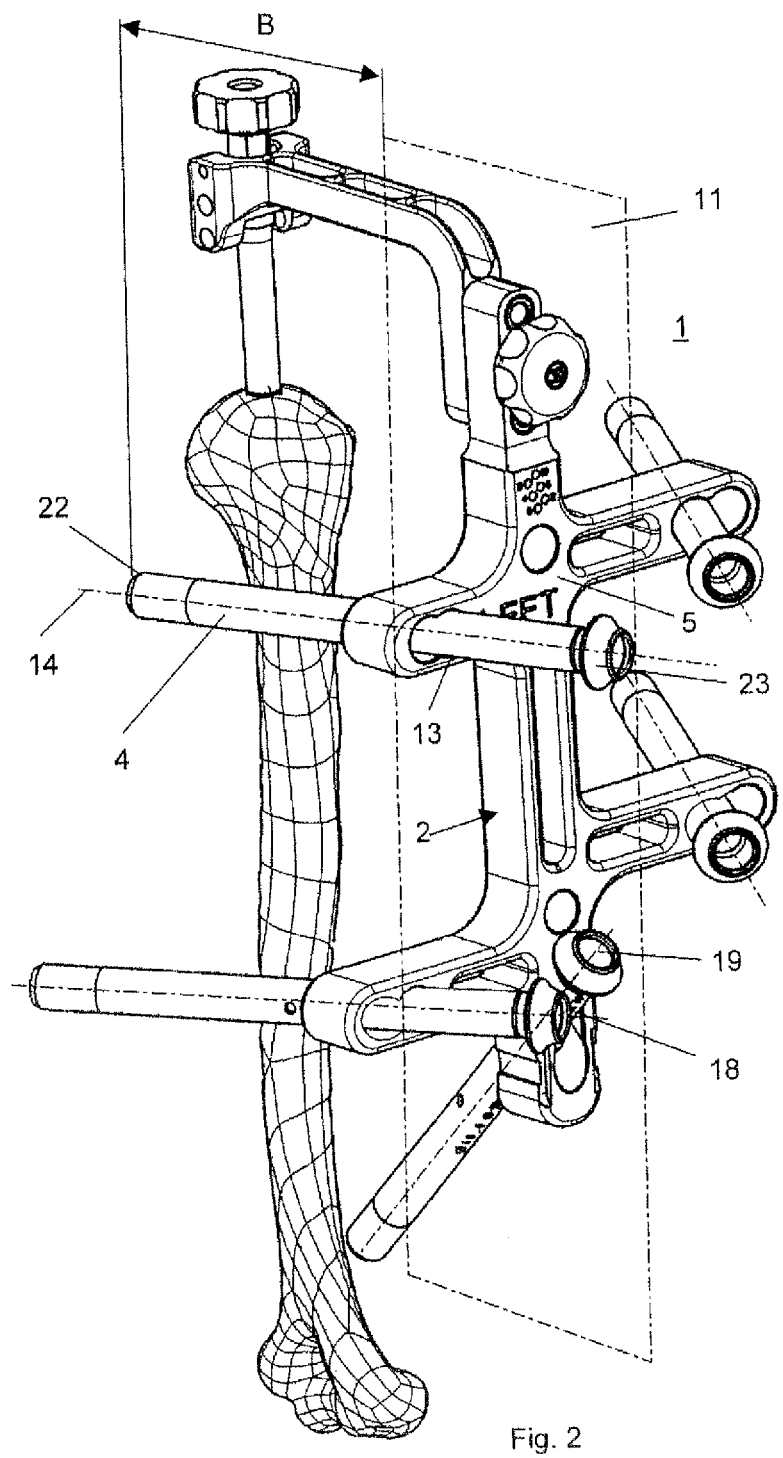
FIG. 2 illustrates a perspective view of the embodiment of FIG. 1 with the drilling bushings inserted in the wrong through holes.

FIGS. 1 and 2 illustrate an embodiment of the intramedullary nail aiming device 1 used with a left side and a right side configuration of an intramedullary nail 8, wherein the intramedullary nail aiming device 1 comprises an aiming plate 2 with a first surface 5, a second surface 6, a distal end 12 and a proximal end 7 attachable to an aiming arm 9 which is fixed to an intramedullary nail 8. In a left side configuration, the first surface 5 faces away from the bone while the second surface 6 faces toward the bone. In a right side configuration, the first surface 5 faces toward the bone while the second surface 6 faces away from the bone. The aiming plate 2 further includes a plurality of compound openings extending through the aiming plate 2 from the first surface 5 to the second surface 6. In a preferred embodiment, the aiming plate 2 includes four compound openings. However, as would be understood by those skilled in the art, any number of compound openings depending on the characteristics of the intramedullary nails to be used with the aiming plate. Each compound opening comprises a first through hole 3 and a second through hole 13 which are open to one another. The first through holes 3 form a first set of four first through holes 3 and the second through holes 13 form a second set of four second through holes 13.

The aiming plate 2 comprises a longitudinal central plate portion 29 extending along a longitudinal axis 15, a first lateral side surface 41 and a second lateral side surface 42. Furthermore, the aiming plate 2 includes two parallel first arms 43 protruding laterally from the first lateral side surface 41 of the central plate portion 29 and two parallel second arms 44 protruding laterally from the second lateral side surface 42 of the central plate portion 29. The first arms 43 and the second arms 44 are staggered along the longitudinal axis 15 and have different lengths. A central plane 11 extending between the proximal end 7 and the distal end 12 and cutting the first and second surfaces 5, 6 is substantially perpendicular to the first and second surfaces 5,6. Additionally, a middle plane 28 orthogonal to the central plane 11 extends through the aiming plate 2 substantially parallel to the first and second surfaces 5,6. Each first through hole 3 defines a first hole axis 10 and each second through hole 13 defines a second hole axis 14, wherein the first and second through holes 3, 13 of each compound opening are arranged in such a way that the first hole axis 10 and the second hole axis 14 intersect one another along the middle plane 28. In the present embodiment the first and second hole axes 10, 14 of the first and second through holes 3, 13 of each compound opening intersect one another along the middle plane 28 at an equal distance E from the central plane 11. The first and second hole axes 10, 14 of the first and second through holes 3, 13 of each compound opening define a plane orthogonal to the middle plane 28 and orthogonal to the central plane 11. Further, the four compound openings are arranged so that the first and second hole axes 10, 14 of each of the first and second through holes 3, 13 of one compound opening define a different plane orthogonal to the middle plane 28 and orthogonal to the central plane 11.

The first through holes 3 are sized and shaped to receive a drill bushing 4 and/or drill bit from the first surface 5 along the central axis 10 aligned with a corresponding locking hole (not shown) in a left side configuration intramedullary nail 8 coupled to the aiming plate 2. The second through holes 13 are sized and shaped to receive a drill bushing 4 and/or drill bit from the second surface 6 along the central axis 14 aligned with a corresponding locking hole in a right side configuration intramedullary nail 8 coupled to the aiming plate 2. The first hole axes 10 of the first through holes 3 converge toward the central plane 11 in a direction from the first surface 5 toward the second surface 6 while the second hole axes 14 of the second through holes 13 diverge from the central plane 11 in the direction from the first surface 5 toward the second surface 6. Thus, each first hole axis 10 of the first through holes 3 forms an angle $\alpha_i$ with the central plane 11 while each second hole axis 14 of the second through holes 13 forms an angle $\beta_i$ with the central plane 11. The present embodiment may comprise four compound openings such that i=1 to 4. If identically positioned anterior and posterior locking holes in the intramedullary nail 8 are used in left side and right side intramedullary nails 8, the angle $\beta_i = -\alpha_i$ for the first and second through holes 3, 13 of each compound opening.

The aiming plate 2 may further comprise an additional compound opening through the central portion 29 of the aiming plate. The additional compound opening includes first and second through holes 16, 18. A first central axis of the 17 of the first through hole 16 corresponds to a locking hole of a left side configuration intramedullary nail 8 while a second central axis 19 of the second through hole corresponds to a locking hole of a right side configuration intramedullary nail 8. Thus, a drill bushing 4 should be inserted through the first through hole 16 along the first central axis 17 from the first surface 5 to the second surface 6 and through the second through hole 18 along the second central axis 19 from the second surface 6 to the first surface 5. The first central axis 17 and the second central axis 19 lie in the central plane 11 and diverge relative to each other in the direction from the first surface 5 towards the second surface 6. Measured in the central plane 11 the first central axis 17 and the second central axis 19 of the additional compound opening form an angle γ.

The intramedullary nail aiming device 1 may further comprises an aiming arm 9 which may be attached to the proximal end of the intramedullary nail 8. The aiming arm 9 has a first end 20 including a first joining mechanism 24 and a second end 21 including a second joining mechanism 25. The first joining mechanism 24 of the aiming arm 9 may be coupled to a third joining mechanism of the aiming plate 2. The first joining mechanism 24 comprises two pins 45, axes of which lie in the central plane 11 and are spaced apart from one another. The third joining mechanism 26 may include bores 46 at a proximal end 7 of the aiming plate 2 for receiving the pins 45 of the first joining mechanism 24 therethrough. Further, the first joining mechanism 24 includes a screw 47 penetrating a respective hole (not shown) in the aiming plate 2 to releasably couple the aiming plate 2 to the aiming arm 9. The second joining mechanism 25 of the aiming arm 9 comprises two further pins 49 and a fastener 48 for releasably coupling the aiming arm 9 to the intramedullary nail 8. The intramedullary nail 8 comprises a fourth joining mechanism 27 including, for example, two lateral holes and a coaxial hole engageable with the second joining mechanism 25 of the aiming arm 9 to allow the releasable coupling of the aiming arm 9 to the intramedullary nail 8 in an aligned position.

As illustrated in FIG. 2, if a drill bushing 4 is inadvertently inserted through the second through holes 13 from the first surface 5 past the second surface 6, while in the aiming plate 2 is in the left side configuration, the drill bushing 4 would not be aligned with any portion of the intramedullary nail 8. Similarly, a drill bushing 4 wrongly inserted into the second through hole 18 of the additional compound opening from the first surface 5 to the second surface 6 would not align with a locking hole of the intramedullary nail 8 and would immediately be recognized as incorrect since the angle γ has a value that can be readily recognized as such.

The embodiment of the intramedullary nail aiming device 1 according to FIGS. 1 and 2 is used with a left side or a right side configuration of an intramedullary nail 8. The method for drilling holes in a bone coaxially to the locking holes of the intramedullary nail 8 comprises the steps of:

1) positioning the aiming plate in the left or right side configuration depending on whether it is to be used with a right side or left side configuration intramedullary nail 8. In the left side configuration, the first surface 5 faces away from the bone while the second surface 6 faces the bone. In the right side configuration, the first surface 5 faces the bone and the second surface 6 faces away from the bone. The aiming plate 2 is then coupled to the intramedullary nail 8 via, for example, the aiming arm 9.

2) inserting a drilling bushing 4 through one of the through holes 3, 13 of the compound opening. When the aiming plate 2 is in the left side configuration, the drilling bushing 4 is inserted through the first through hole 3 and when the aiming plate 2 is in the right side configuration, the drill bushing is inserted through the second through hole 13.

3) checking whether the drilling bushing 4 has been inserted through a correct one of the first and second through holes 3, 13 (e.g., through the first through hole 3 in the case of a left side intramedullary nail 8 or through the second hole 13 in the case of a right side intramedullary nail 8). When the drilling bushing 4 has been inserted in a wrong one of the through holes 3, 13 (e.g., through the second through hole 13 in the case of a left side intramedullary nail 8 or through a first through hole 3 in the case of a right side intramedullary nail 8), inserting the drilling bushing 4 into the other of the through holes 3, 13 and repeating step 3); and 4) when the drilling bushing 4 has been inserted in a correct one of the through holes 3, 13, drilling at least one hole in a bone into which the intramedullary nail 8 has been inserted using the drilling bushing 4 for guiding a drill bit.

Alternatively, the above steps 2)-4) can be performed for each of the first or second through holes 3, 13 separately and repeated for the respective number of first or second through holes 3, 13 to be applied in the procedure.

FIGS. 3 to 5 show another embodiment of the aiming device 1 mounted to an intramedullary nail 8 configured as a universal intramedullary nail 8 with only one configuration for both left side and right side bones. Depending on the application of the universal intramedullary nail 8 for the left side or the right side bone, the locking of the intramedullary nail 8 in the bone does not necessarily include insertion of a locking screw 40 in every one of the proximal and distal locking holes 31, 32 of the intramedullary nail 8. In some cases (for anatomical reasons) one or more of the proximal and distal locking holes 31, 32 of the intramedullary nail 8 will not be used for insertion of a locking screw 40. For example, when inserting a universal intramedullary nail 8 into the proximal humerus, a locking screw 40 is often not inserted into the most anterior proximal locking hole 33 (FIGS. 3 and 5) because it might penetrate the biceps tendon. When using a universal intramedullary nail 8 on the left side humerus (FIG. 3) the second locking screw 40 from the proximal end 35 of the universal intramedullary nail 8 may be problematic. Similarly, when inserting a universal intramedullary nail 8 in the right side humerus (FIGS. 4 and 5), the third locking screw 40 from the proximal end 35 of the universal intramedullary nail 8 may be problematic (FIG. 5).

The embodiment of the intramedullary nail aiming device 1 illustrated in FIGS. 3 to 5 differs from the embodiment of FIGS. 1 and 2 only in that the aiming plate 2 includes only one arm 44 protruding from the second lateral side 42 and the aiming plate 2 comprises only one compound opening including a first through hole 3 with a first hole axis 10 and a second through hole 13 with a second hole axis 14. Additionally, the aiming plate 2 includes a number of central through holes 50 extending through the central portion 29 of the aiming plate 2 at different distances from the proximal end 7 of the aiming plate 2. The central through holes 50 have hole axes lying in the central plane 11 and extending orthogonally to the middle plane 28. Thus, locking screws 40 inserted into the proximal locking holes 31 extend parallel to the frontal plane of the patient. The first and second through holes 3, 13 are arranged in the arm 44. Further, the first and second hole axes 10, 14 of the first and second through holes 3, 13 of the compound opening are arranged in different planes orthogonal to the middle plane 28 and orthogonal to the central plane 11. Therefore, in the embodiment of the aiming plate 2 of FIGS. 3 to 5 the first and second hole axes 10, 14 are skew lines. The first through hole 3 is suitable for receiving a drill bushing 4 from the left side 5 in a predetermined direction coinciding with the corresponding third locking hole 31 from the proximal end 35 of the universal intramedullary nail 8 (FIG. 3). The second through hole 13 is suitable for receiving a drill bushing 4 from the right side 6 (FIG. 4) in a predetermined direction coinciding with the corresponding second locking hole 31 of the universal intramedullary nail 8. As illustrated in FIG. 5, if the drill bushing 4 is inserted through the first through hole 3 from the second surface 6 to the first surface 5, the drill bushing is not aligned with any portion of the intramedullary nail 8 so that the surgeon realizes at one glance that the drill bushing 4 is inserted in the wrong hole.

The embodiment of the intramedullary nail aiming device 1 shown in FIGS. 3 to 5 is configured for use with a universal intramedullary nail 8 having only one configuration for both left and right side bones. The method for drilling holes in a bone coaxially to the desired locking holes 31, 32 of the intramedullary nail 8 comprises the steps of:

1) positioning the aiming plate 2 in the left or right side configuration depending on whether intramedullary nail 8 is being used to treat a left side or a right bone and fixing the aiming plate 2 to the intramedullary nail 8;
2) inserting a drilling bushing 4 into one of the first and second through holes 3, 13;
3) checking whether the drilling bushing 4 has been inserted in a correct through hole 3, 13 (i.e., the first through hole 3 when the universal nail is inserted in a left side bone or in a second through hole 13 when the universal nail is inserted in a right side bone). If the drilling bushing 4 has been wrongly inserted in the second through hole 13 in case of a left side bone or wrongly in the first through hole 3 in case of a right side bone, the drilling bushing 4 is inserted into the other through hole 3, 13 of the first respectively second through holes 3, 13. If the drilling bushing 4 has been correctly inserted in the first through hole 3 in case of using a left side bone or correctly inserted in the second through hole 13 in case of a right side bone, the user drills at least one hole in a bone into which the intramedullary nail 8 has been inserted using the drilling bushing 4 to guide the drill bit.

The embodiment of the intramedullary nail aiming device 1 shown in FIGS. 1 to 5, is aligned with the intramedullary nail to ensure that a correct through hole for receiving a tool is aligned with a desired feature of an implant. To achieve this alignment, a method can be used, which has the steps of:

a) identifying a type of implant to be coupled to an aiming plate;
b) determining a correct configuration of an aiming plate according to the identified implant type; and
c) coupling the aiming plate to an implant of the identified implant type in the determined correct configuration;

The determined correct configuration is one of the left side configuration or right hand side configuration described previously. The same applies for the universal intramedullary nail shown in FIGS. 3 to 5. Markings "LEFT" and "RIGHT" on opposed surfaces of the aiming plate 1 are also used to determine the correct configuration. That is, the marking "LEFT" indicates the surface a user should see when the other surface is facing towards the nail in the left side configuration, and the marking "RIGHT" indicates the surface a user should see when the other surface is facing towards the nail in the right side configuration.

Although the invention and its advantages have been described in detail, it should be understood that various changes, substitutions, and alterations may be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

What is claimed is:

1. An aiming plate configured to orient one or more drill guides toward target features of an intramedullary nail, the aiming plate comprising:
an aiming plate body elongate along a longitudinal direction, the aiming plate body defining a first surface and a second surface opposite the first surface along a transverse direction that is perpendicular to the longitudinal direction, and a first through hole configured to receive a respective one of the one or more drill guides, the first through hole extending along a first hole axis from the first surface to the second surface, the implant body defining a second through hole configured to receive another of the respective drill guides, the second through hole positioned adjacent to the first through hole, the second through hole extending along a second hole axis from the first surface to the second surface, wherein the first hole axis intersects the second hole axis,
the aiming plate body configured to attach to the intramedullary nail in either a first orientation or a second orientation, the first orientation defined as when the first surface is oriented toward the intramedullary nail and the second orientation defined as when the second surface is oriented toward the intramedullary nail,
wherein when the aiming plate is attached to the intramedullary nail in the first orientation, one of the first and second hole axes is directed toward the target feature of the intramedullary nail and the other of the first and second hole axes is directed away from the intramedullary nail along a lateral direction that is perpendicular to both the longitudinal direction and the transverse direction.

2. The aiming plate as recited in claim 1, wherein the aiming plate body defines a central axis, a proximal end, and a distal end spaced from the proximal end along the central axis, the aiming plate body including a central portion that extends along the central axis and at least one arm that extends from the central portion along a direction that is transverse to the central axis, wherein at least one of the central portion and the at least one arm defines the first and second through holes.

3. The aiming plate as recited in claim 2, wherein the at least one arm is a first arm and a second arm, and the first arm includes the first through hole and the second arm includes the second through hole.

4. The aiming plate as recited in claim 1, wherein when the aiming plates is attached to the intramedullary nail in the first orientation, the first axis intersects the intramedullary nail and the second axis does not intersect the intramedullary nail.

5. The aiming plate as recited in claim 4, wherein when the aiming plate is attached to the intramedullary nail in the second orientation, the second axis intersects the intramedullary nail and the first axis does not intersect the intramedullary nail.

6. The aiming plate as recited in claim 5, further comprising a reversible attachment mechanism configured to permit attachment the aiming plate to the intramedullary nail so as to orientate the aiming plate toward the intramedullary nail in the first orientation or the second orientation.

7. The aiming plate as recited in claim 1, wherein the first and second through hole axes intersect at a point located between the first and second surfaces of the aiming plate body.

8. The aiming plate of claim 1, wherein when the aiming plate is coupled to the intramedullary nail in the first orientation, the first hole axis intersects the target feature of the intramedullary nail and the second hole axis is directed away from the target feature of the intramedullary nail, and when the aiming plate is coupled to the intramedullary nail in the second orientation, the second hole axis intersects target feature on the intramedullary nail, and the first hole axis is directed away from the target feature of the intramedullary nail.

9. The aiming plate of claim 1, wherein the first through hole is open to the second through hole.

* * * * *